(12) United States Patent
Li

(10) Patent No.: US 7,079,256 B2
(45) Date of Patent: Jul. 18, 2006

(54) INTERFEROMETRIC OPTICAL APPARATUS AND METHOD FOR MEASUREMENTS

(76) Inventor: Chian Chiu Li, 580 N. Mary Ave., Sunnyvale, CA (US) 94085

( * ) Notice: Subject to any disclaimer, the term of this patent is extended or adjusted under 35 U.S.C. 154(b) by 421 days.

(21) Appl. No.: 10/637,426

(22) Filed: Aug. 9, 2003

(65) Prior Publication Data

US 2005/0030548 A1 Feb. 10, 2005

(51) Int. Cl.
 *G01B 11/02* (2006.01)
(52) U.S. Cl. .................................. 356/497
(58) Field of Classification Search ................ 356/497, 356/498, 499, 521
 See application file for complete search history.

(56) References Cited

U.S. PATENT DOCUMENTS

| | | |
|---|---|---|
| 5,121,378 A | 6/1992 | Hirose et al. |
| 5,841,583 A | 11/1998 | Bhagavatula |
| 5,978,109 A | 11/1999 | Kato et al. |
| 6,246,477 B1 | 6/2001 | Feldman |
| 2004/0160611 A1* | 8/2004 | Li .............................. 356/521 |

OTHER PUBLICATIONS

H. Ando, T. Yokota, K. Tanoue, "Optical Head with Annular Phase—Shifting Apodizer," Japanese Journal of Applied Physics, 1993, vol. 32, pp. 5269-5276.

* cited by examiner

*Primary Examiner*—Gregory J. Toatley, Jr.
*Assistant Examiner*—Michael A. Lyons

(57) ABSTRACT

In order to improve lateral resolution of scanning optical devices, a low-coherence sample beam is divided into beam portions by wavefront division and one of the beam portions is phase delayed relative to the other portions. The sample beam is focused on and reflected by an object. The reflected beam is coupled with a reference beam. The phase retardation is large enough that interference occurs exclusively between the phase delayed beam portion and the reference beam. The phase delayed beam portion can be used as a virtual beam within the sample beam in optical measurements. The virtual beam has a virtual beam spot that is smaller than the sample beam spot.

22 Claims, 7 Drawing Sheets

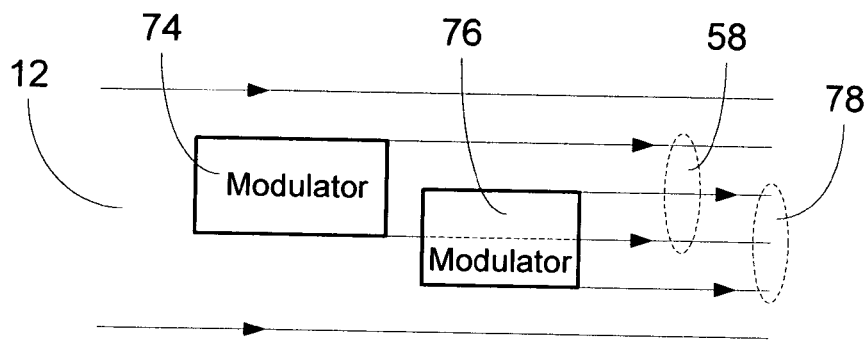
FIG. 2-C
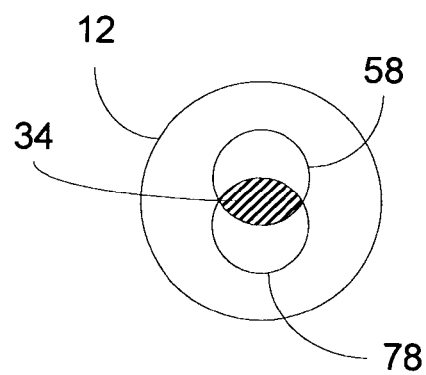
FIG. 2-D
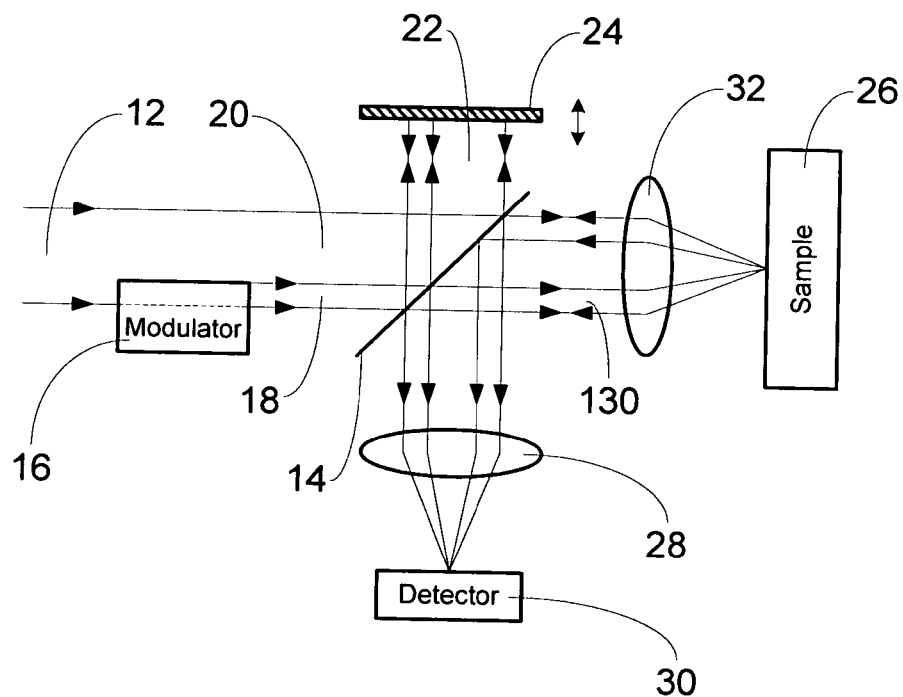
FIG. 3

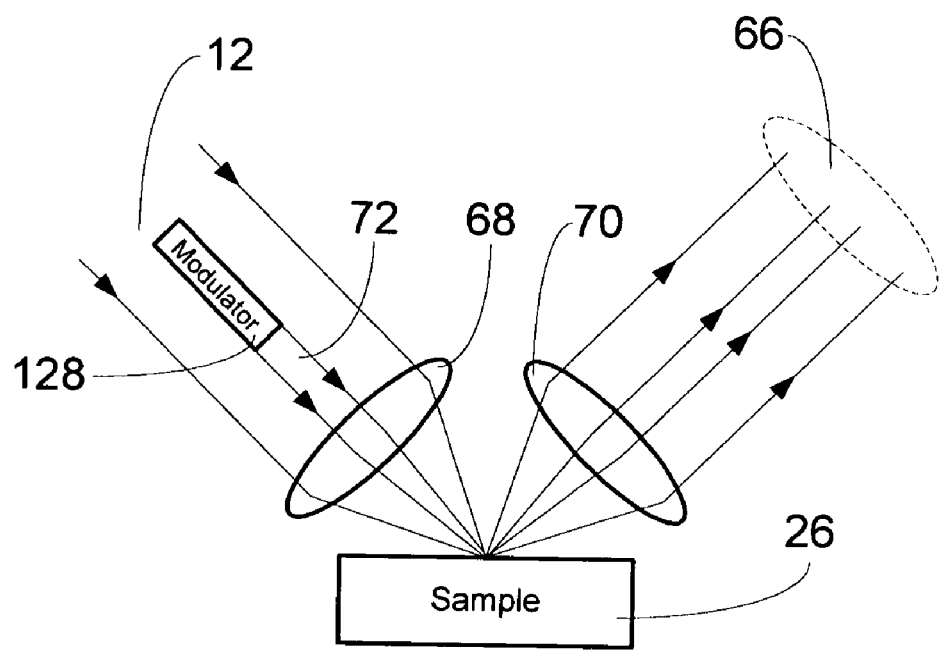
FIG. 10-A
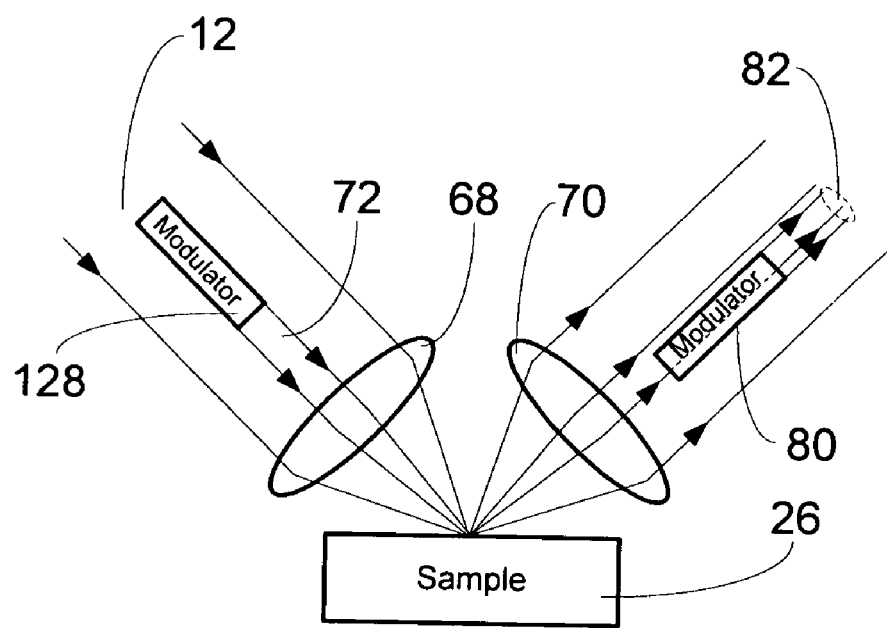
FIG. 10-B

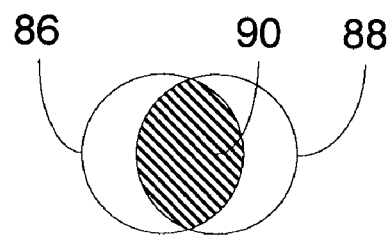
FIG. 10-C
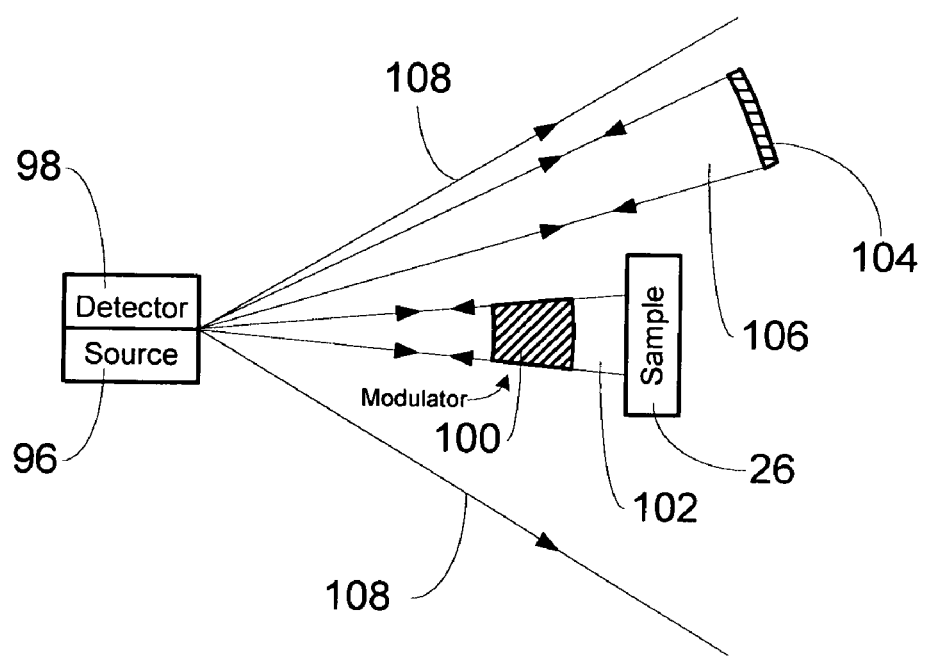
FIG. 11-A
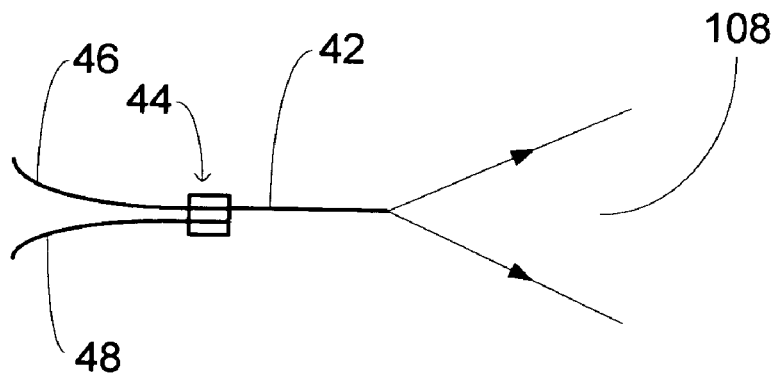
FIG. 11-B

INTERFEROMETRIC OPTICAL APPARATUS AND METHOD FOR MEASUREMENTS

FEDERALLY SPONSORED RESEARCH

Not applicable

SEQUENCE LISTING OR PROGRAM

Not applicable

CROSS REFERENCE TO RELATED APPLICATION

This application is related to my U.S. regular patent application Ser. No. 10/367,510, now allowed, which is incorporated herein by reference.

BACKGROUND—FIELD OF INVENTION

This invention relates to optical measurements, more particularly to an interferometric device for use in a scanning optical microscope, a scanning optical profiler, an optical data storage system, or an optical coherence tomographic system.

BACKGROUND—DESCRIPTION OF PRIOR ART

A scanning optical microscope is used for investigation and inspection of products and samples in semiconductor, optical, biological, and medical fields. Usually a light beam is focused to create a beam spot on a sample. Reflection from the spot is collected and analyzed. Spots of a specific sample region are scanned in this way and then stitched (combined electronically) to form an image. The microscope's lateral resolution, i.e., resolution in a plane perpendicular to the beam's propagation direction, is determined by a spot size or diameter of the focused beam. The smaller the spot size, the higher the lateral resolution.

Another instrument, which has applications in semiconductor and magnetic data storage industries, is scanning optical profiler. It measures a surface profile with high precision. For a typical scanning optical profiler, at least one light beam is focused on a surface. Reflection from the beam spot is then utilized to obtain height information through an interference method. A profile is obtained after the surface is scanned. Again, the spot size of the focused beam determines the profiler's lateral resolution.

In yet another application, optical data storage systems, such as CD/DVD players, have become an indispensable part of our daily lives. An optical data storage system relies on a readout beam to acquire stored information from a series of pits on an optical disc. The size of each pit is designed according to the spot diameter of the focused readout beam. The smaller the spot diameter is, the smaller the pit, then the greater the data density and the larger the disc's storage capacity.

Therefore a focused beam with a smaller spot size is desirable in many fields. It results in higher lateral resolution for a scanning microscope and profiler, and larger capacity for an optical disc.

However, the spot size or diameter of a focused beam can't be reduced arbitrarily and infinitely. In fact, the diameter of a focused beam is proportional to the wavelength of the beam and inversely proportional to the numerical aperture (NA) of the focus lens. On the one hand, a shorter wavelength or larger NA is needed for a thinner focused beam. On the other hand, the wavelength is limited in the optical range and the NA of a lens can't go beyond a certain value. Thus a focused beam has an inherent limitation on its diameter, the so-called diffraction limit.

Efforts have been made to provide a smaller beam spot than the diffraction limit. For example, Kato et al. describe a phase plate in U.S. Pat. No. 5,978,109 (1999). The phase plate divides a transmitted beam into different beam portions through wavefront division. Each beam portion is phase delayed by a certain value. When the beam is focused on an object, destructive interference makes the focusing spot smaller than the limit.

Another method uses a shield to obstruct a central part of a circular beam to create an annular beam. When the annular beam is focused, the resulting spot size is reduced beyond the diffraction limit. Examples can be found in U.S. Pat. No. 5,121,378 (1992) to Hirose et al.

In the above methods, the lateral alignment, which is between the beam and the shield or the phase plate in a plane perpendicular to the beam's propagation direction, must be accurate. Thus current techniques to reduce beam spot size suffer from sensitivity to lateral misalignment.

Optical coherence tomography (OCT) is an imaging technology capable of measuring three-dimensional structures of highly scattering media, such as a variety of biological tissues. It has great potential in biomedical applications. In an OCT, a beam from a light source is split into sample and reference beams. The sample beam is focused inside a highly scattering medium and the reference beam is directed to a reference reflector. The reflected sample and reference beams are coupled to produce interference signals which carry information of a focal region. An OCT has a similar scanning mechanism to that used by a scanning microscope or profiler.

An OCT usually has a low-coherence light source. Compared to a coherent light source, the low-coherence source emits a beam that has a short coherence length and a broad spectral width. Interference between the sample and reference beams happens only when their optical path length difference is within the beam's coherence length. The low-coherence interference reaches maximum intensity when the two optical path lengths are matched. Thus an OCT's axial resolution, which is in its sample beam's propagation direction, is determined by the beam's coherence length. The shorter the coherence length, the higher the OCT's axial resolution.

For a reference path length, interference signals reveal sample information only from a particular region which has a matching sample path length. The region is usually chosen to be where the beam is focused and within the Rayleigh range, which is half of depth of focus. So the Rayleigh range defines an OCT's axial scan range. By adjusting reference path length, layered information within the Rayleigh range is observed. In practice, a longer axial scan range is often desired. But depth of focus is proportional to diameter of the focused beam, or the lateral resolution. To date, a compromise has to be made between an OCT's axial scan range and its lateral resolution.

OBJECTS AND ADVANTAGES

Accordingly, several main objects and advantages of the present invention are:

a). to provide a beam with smaller spot size for use in optical devices;

b). to provide a device as a scanning optical microscope, a scanning optical profiler, or a readout system in optical data storage, which has an improved lateral resolution and is insensitive to the lateral misalignment;

c). to provide a device as an OCT which has an improved lateral resolution without sacrificing axial scan range.

Further objects and advantages will become apparent from a consideration of the drawings and ensuing description.

SUMMARY

In accordance with the present invention, an interferometric optical device has a low-coherence sample beam that is divided into beam portions through wavefront division. At least one beam portion is substantially phase delayed relative to the other portions. The sample beam is focused on a sample and the reflected beam is coupled with a reference beam for generating interference. Due to the low coherence, only the phase delayed beam portion, which has a longer optical path length than the other beam portions, interferes with the reference beam. Thus the phase delayed beam portion can be used as a virtual beam within the sample beam. The resulting virtual beam spot is smaller than the sample beam spot.

The virtual beam has applications in scanning optical microscopes, scanning optical profilers, optical data storage systems, and OCTs. It improves lateral resolution in a way that is insensitive to lateral misalignment and doesn't reduce the axial scan range.

ABBREVIATIONS $\Delta n$ Difference of refractive index between the modulator material and the ambient medium L Modulator length along the beam's propagation direction NA Numerical Aperture OCT Optical Coherence Tomography

DRAWING FIGURES

FIG. 1 is a schematic diagram showing an embodiment of the interferometric optical device according to the invention.

FIG. 2-A is a schematic cross-sectional view showing a virtual beam inside a beam according to the invention.

FIG. 2-B is a schematic diagram showing a virtual beam spot inside a beam spot according to the invention.

FIGS. 2-C and 2-D are schematic diagrams showing two spatial phase modulators generating an overlap of beam portions according to the invention.

FIGS. 3 and 4 are schematic diagrams showing two embodiments according to the invention.

Figure 1:
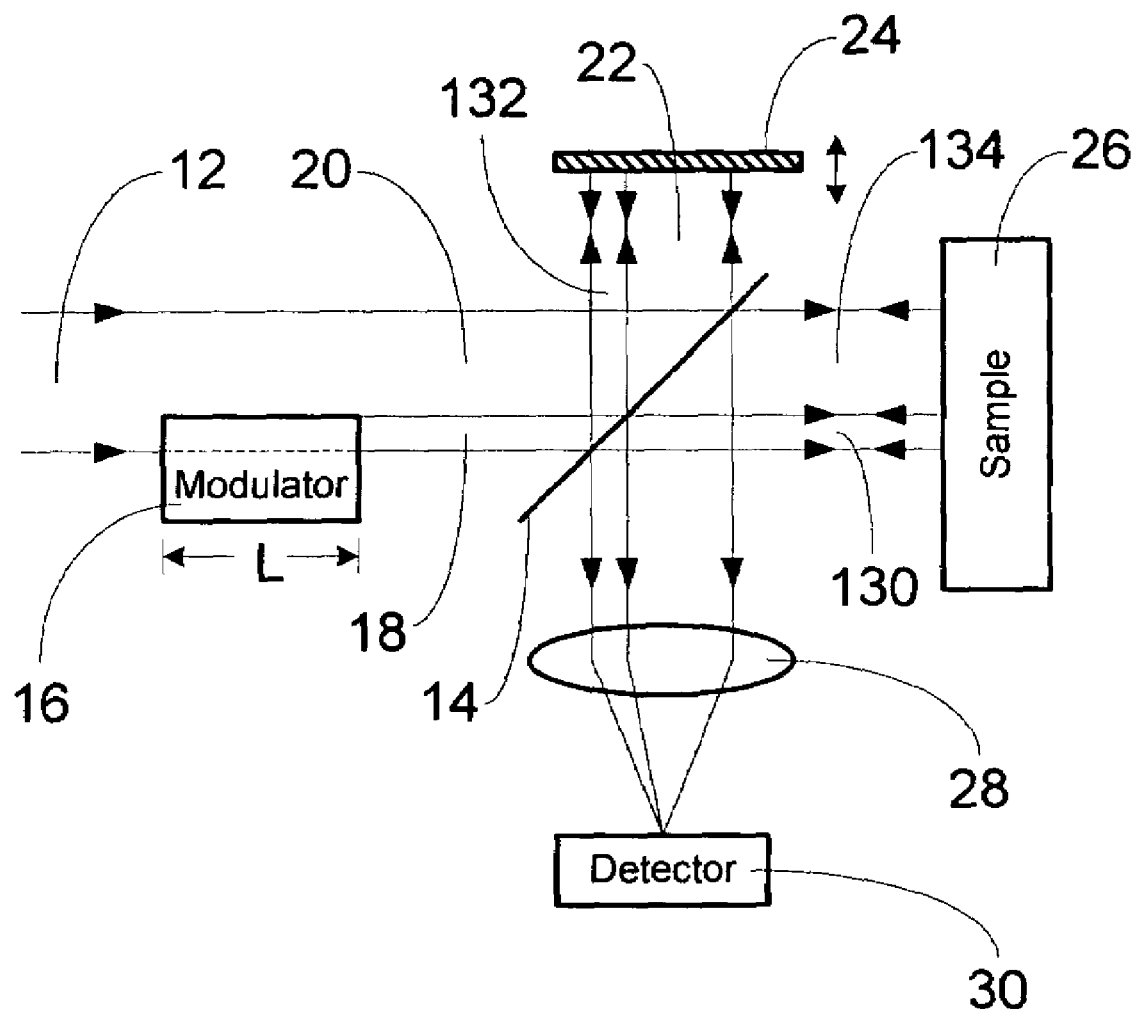

FIGS. 10-A and 10-B are schematic diagrams showing embodiments with an additional lens system for receiving reflection from a sample according to the invention.

10-C is a schematic diagram showing an overlapping area of two virtual beam spots according to the invention.

FIGS. 11-A and 11-B are schematic diagrams showing two embodiments according to the invention.

REFERENCE NUMERALS IN DRAWINGS 12 collimated beam
14 beam splitterg
16 spatial phase modulator
18 beam portion
20 beam portion
22 beam portion
24 reflector
26 sample
28 lens system
30 detector
32 lens system
34 beam portion
36 beam splitter
38 lens system
40 single-mode fiber
42 single-mode fiber
44 fiberoptic coupler
46 single-mode fiber
48 single-mode fiber
50 lens system
52 partial reflector
54 beam splitter
56 reflector
58 beam portion
60 beam portion
62 spatial phase modulator
64 spatial phase modulator
66 collimated beam
68 lens system
70 lens system
72 beam portion
74 spatial phase modulator
76 spatial phase modulator
78 beam portion
80 spatial phase modulator
82 beam portion
84 beam portion
86 virtual beam spot
88 virtual beam spot
90 overlapping area
92 beam spot
94 virtual beam spot
96 light source
98 detector
100 spatial phase modulator
102 beam portion
104 reflector
106 beam portion
108 beam
110 partial reflector
112 reflector
114 phase modulator
116 beam splitter
118 beam splitter
120 spatial phase modulator
122 beam portion
124 beam portion 126 beam portion
128 spatial phase modulator
130 beam portion
132 beam portion
134 beam portion
136 reflector

DESCRIPTION—FIG. 1—INTERFEROMETRIC OPTICAL DEVICE

FIG. 1 illustrates schematically an embodiment according to the invention. A collimated beam 12, preferably having a short coherence length, passes through a spatial phase modulator 16. Modulator 16 is made of up a transparent material whose refractive index is bigger than the ambient refractive index. The modulator divides beam 12 into beam portions 18 and 20. Portion 20 passes through the ambient medium, while portion 18 is transmitted through the modulator and is phase delayed relative to portion 20. The optical path length difference between portions 18 and 20 is determined by the product of L and □n, where L is the length along which portion 18 travels in modulator 16 and □n is the refractive index difference between the modulator material and the ambient medium. Assume that the path length difference is much larger than the beam's coherence length. Then portion 18 can interfere with a reference beam exclusively due to low-coherence interference.

After being processed by modulator 16, beam 12 enters a Michelson interferometer, which includes a beam splitter 14, an adjustable reference reflector 24, and a reflective sample 26 as the other reflector in a configuration as in FIG. 1. Splitter 14 splits beam 12 into reference and sample beams. The reference beam is directed to reflector 24 by reflection and the sample beam is transmitted toward sample 26. The splitting generates four beam portions, among which portions 22 and 134 result from portion 20, and portions 132 and 130 from portion 18. When the sample beam impinges onto sample 26, it is reflected back to splitter 14. Meanwhile, the reference beam is also reflected back to splitter 14 by reflector 24. The reflected sample and reference beams or the four portions are combined by splitter 14 and focused by a lens system 28 on a detector 30, which usually is a photodetector that converts light into electronic signals.

Assume that the surface of sample 26 introduces a relatively small path length change. Then optical path length of each beam portion depends mainly on three factors: modulator 16 and the position of sample 26 and reflector 24. Assume modulator 16 and the position of sample 26 are fixed. When reflector 24 is tuned so that portions 22 and 130 have a matching path length, portion 134 has a phase difference relative to portion 22 or 130 which equals the quantity caused by modulator 16, and portion 132 has a phase difference twice that value. Therefore portion 130 can exclusively interfere with portion 22, which represents the reference beam. As a result, portion 130 can be used as a virtual beam within the sample beam.

Since the virtual beam, or portion 130 is part of the sample beam, it is thinner and has a smaller beam spot than the sample beam. Furthermore, the spot size of the virtual beam is not affected by the lateral position of portion 130. Thus the virtual beam is insensitive to lateral misalignment of modulator 16.

The embodiment of FIG. 1 works in the same way when reflector 24 is fixed at a certain position and modulator 16 produces a tunable phase retardation, assuming that the phase retardation is maintained substantially large during tuning.

The components of FIG. 1 and the remaining embodiments are well known to those skilled in the art. Real values and parameters can easily be selected according to the nature of sample 26 and the task to be performed. For example, sample 26 can be a silicon wafer or a metal, beam 12 can have a wavelength of 1300 nanometer, etc. Other sample types and parameters and values are possible.

FIGS. 2-A–2-D—SPATIAL PHASE MODULATOR AND BEAM PORTIONS

FIG. 2-A shows schematically an example where a spatial phase modulator 120 divides beam 12 into portions 122 and 124 in a cross-sectional view in a plane perpendicular to the beam's propagation direction. Portion 122 can be used as a virtual beam which produces a virtual beam spot 94 inside a beam spot 92 on a surface, as shown schematically in FIG. 2-B. Since a virtual beam spot is part of a beam spot, the former is smaller than the latter.

A spatial phase modulator divides a beam into beam portions by wavefront division and phase delays one portion relative to the others. The phase delayed portion can be in any position inside a beam. Usually a phase delay is generated when beam portions are transmitted through elements with different refractive indexes, or along different paths in the same media.

To avoid wavefront distortion due to diffraction, a phase delayed beam portion has geometric features which are much larger than the beam's wavelength in a plane perpendicular to the beam's propagation direction. For the same reason, the beam should have a diameter much larger than its wavelength.

A beam doesn't need to be collimated before division, although a collimated beam makes it easier to process than a divergent or a convergent beam.

Two spatial phase modulators can process a beam in sequence, as shown schematically in FIG. 2-C. Modulators 74 and 76 phase delay portions 58 and 78 of beam 12, respectively. Since the two portions have an overlapping region, there exists a beam portion which is phase delayed by both modulators. FIG. 2-D illustrates schematically a portion 34 which corresponds to the overlapping region of portions 58 and 78 in a cross-sectional view in a plane perpendicular to the beam's propagation direction.

Compared to portions 58 and 78, portion 34 yields a smaller virtual beam with a smaller virtual beam spot.

When a phase delayed beam portion is out of phase with its adjacent portions, destructive interference occurs around the boundary regions. The destructive interference deforms a virtual beam spot. Preferably, the beam portion is not only phase delayed substantially, but also kept in phase with the other portions.

The dimension and material of a spatial phase modulator can easily be selected by those skilled in the art according to the nature of the beam and the task to be performed, e.g. liquid crystals or other electro-optical materials can be used to make a tunable modulator, various glass materials that have a refractive index around 1.5 can be used for a fixed modulator, etc.

Figure 4:
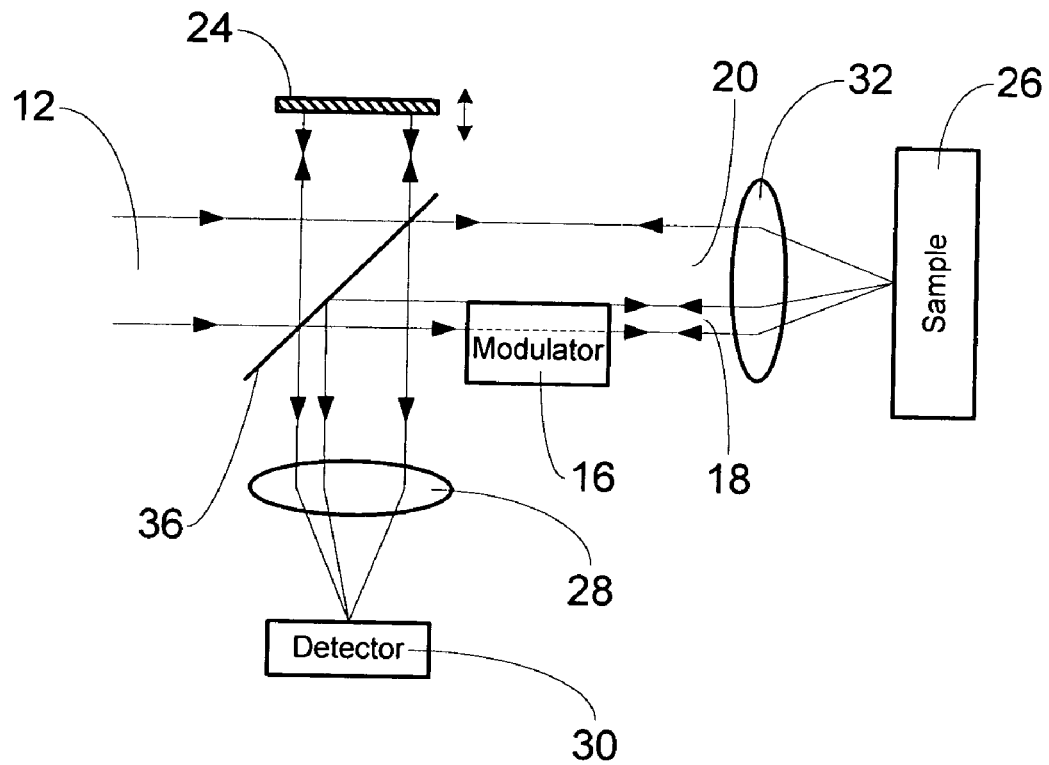

FIGS. 3 and 4—DEVICES FOR MICROSCOPES, READOUT SYSTEMS, AND OCTS

For many measurements, a focused sample beam is desirable. FIG. 3 shows schematically another embodiment, which adds a focus lens system 32 between splitter 14 and sample 26 of the Michelson interferometer in FIG. 1. As in FIG. 1, after passing through splitter 14, portion 18 becomes portion 130. Portion 130 represents a virtual beam, and it is focused by lens system 32 on a virtual beam spot inside a focused beam spot on the surface of sample 26 (the spots are not shown in FIG. 3).

The virtual beam spot can be used to improve lateral resolution for scanning optical microscopes and readout systems in optical data storage.

In OCT applications, sample 26 is a highly scattering medium and the sample beam is focused in a focal volume inside the medium. Within the focal volume, portion 130 creates a virtual volume. The reflected portion 130 contains reflection from different sample depths within the virtual volume. Adjusting reflector 24 can result in an exclusive interference between the reference beam and part of portion 130 that is reflected from a certain depth in the virtual volume. The axial scan range remains unchanged, but the virtual volume improves the OCT's lateral resolution.

The position of the virtual beam inside the sample beam is relatively non-critical in a scanning optical device. Thus the device is insensitive to the lateral misalignment between the beam and the spatial phase modulator.

FIG. 4 shows schematically another embodiment. A beam splitter 36 splits collimated beam 12 into reference and sample beams. The reference beam is reflected toward adjustable reference reflector 24 and reflected back to splitter 36. The sample beam passes through splitter 36 and is divided into beam portions 18 and 20 by modulator 16. The sample beam is then focused onto sample 26 by lens system 32. The reflected sample beam is collimated by lens system 32 and is transmitted through modulator 16 again. Finally the reflected reference and sample beams are combined by splitter 36 and focused on detector 30.

The difference between embodiments of FIGS. 3 and 4 is that part of the phase delayed portion is transmitted through modulator 16 twice in the latter case. Thus in the embodiment of FIG. 4, the reference reflector is adjusted for an exclusive interference between the reference beam and part of portion 18 which is phase delayed twice. Portion 18 works as a virtual beam in the same way as portion 130 of FIG. 3.

Figure 5:
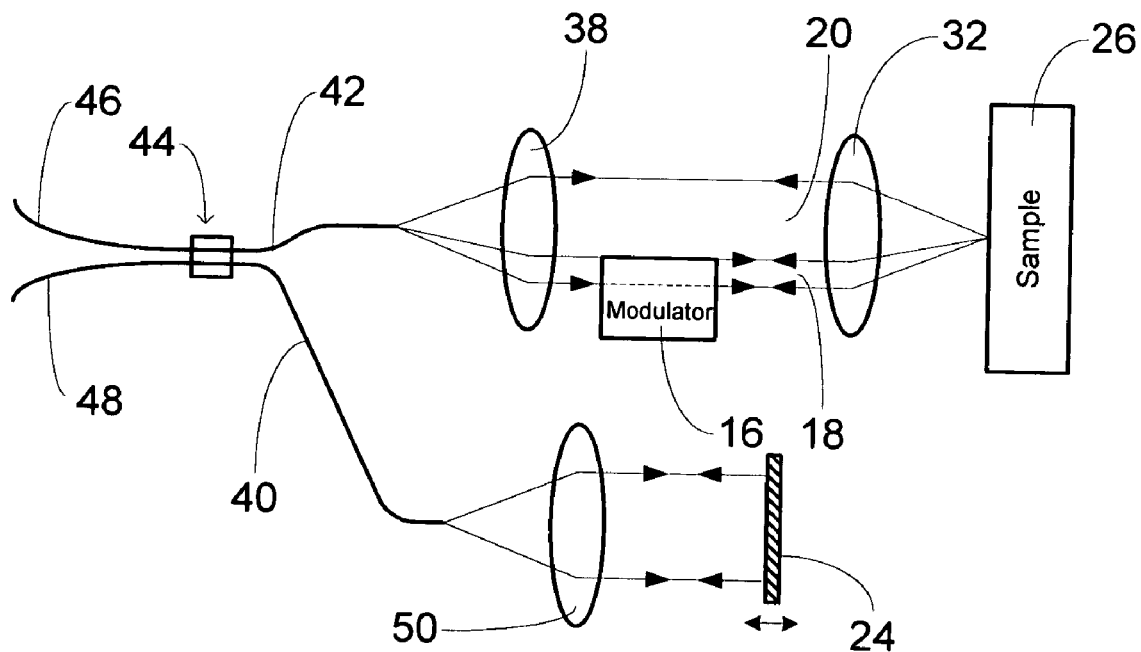
FIGS. 5 and 6 are schematic diagrams showing two embodiments employing fiberoptic components according to the invention.
Figure 6:
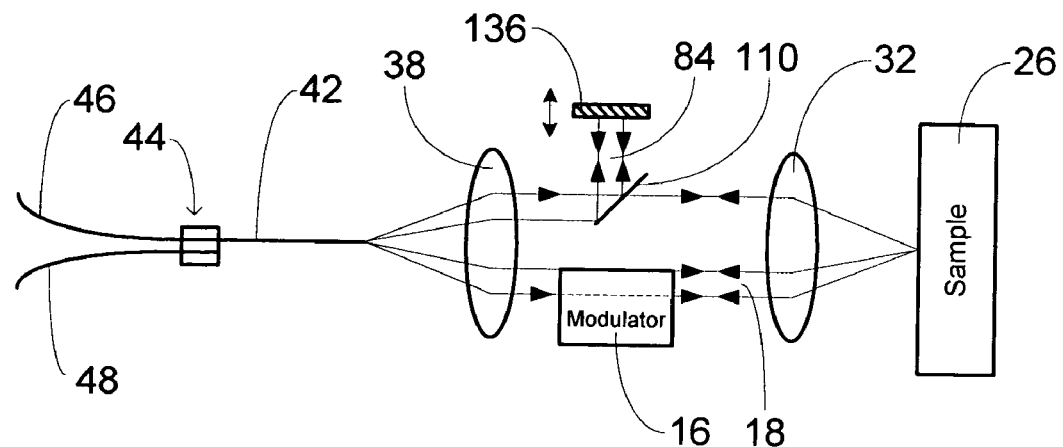

FIGS. 5 and 6—DEVICES EMPLOYING FIBEROPTIC COMPONENTS

FIG. 5 illustrates schematically an embodiment that employs fiberoptic components. The embodiment of FIG. 5 is similar to that of FIG. 4, except that light travels partially along single-mode optical fibers and a fiberoptic coupler 44 replaces splitter 36. Here fibers 46 and 48 lead to a light source and a detector (the light source and detector are not shown in FIG. 5), respectively. Fiber 40 carries a reference beam and fiber 42 a sample beam. Coupler 44 couples fibers 46 and 48 with fibers 40 and 42. Lens systems 38 and 50 collimate the beams emerging from fibers 42 and 40, respectively.

FIG. 6 shows schematically another embodiment. Compared to the embodiment of FIG. 5, the reference and sample beams are portions of one beam and travel along the same fiber, fiber 42. The reference beam is generated through wavefront division instead of amplitude division. Similar to the embodiment of FIG. 5, fibers 46 and 48 lead to a light source and a detector (not shown in FIG. 6), respectively. Coupler 44 couples fiber 42 with fibers 46 and 48. After a beam from fiber 42 is collimated, a beam portion is diverted by a partial reflector 110 and becomes a portion 84, and the rest of the beam becomes a sample beam. Portion 84, working as a reference beam, is reflected back by an adjustable reflector 136 and then by reflector 110. The sample beam is processed by modulator 16 in the same way as in FIG. 5.

The embodiments of FIGS. 5 and 6 enable separation among a light source, a detector, and a sample, and thus provide convenience in applications. Between the two embodiments, the latter embodiment is less sensitive to environmental changes than the former, since its sample and reference beams are transmitted along one fiber.

FIG. 7—DEVICE EMPLOYING MACH-ZEHNDER INTERFEROMETER

Figure 7:
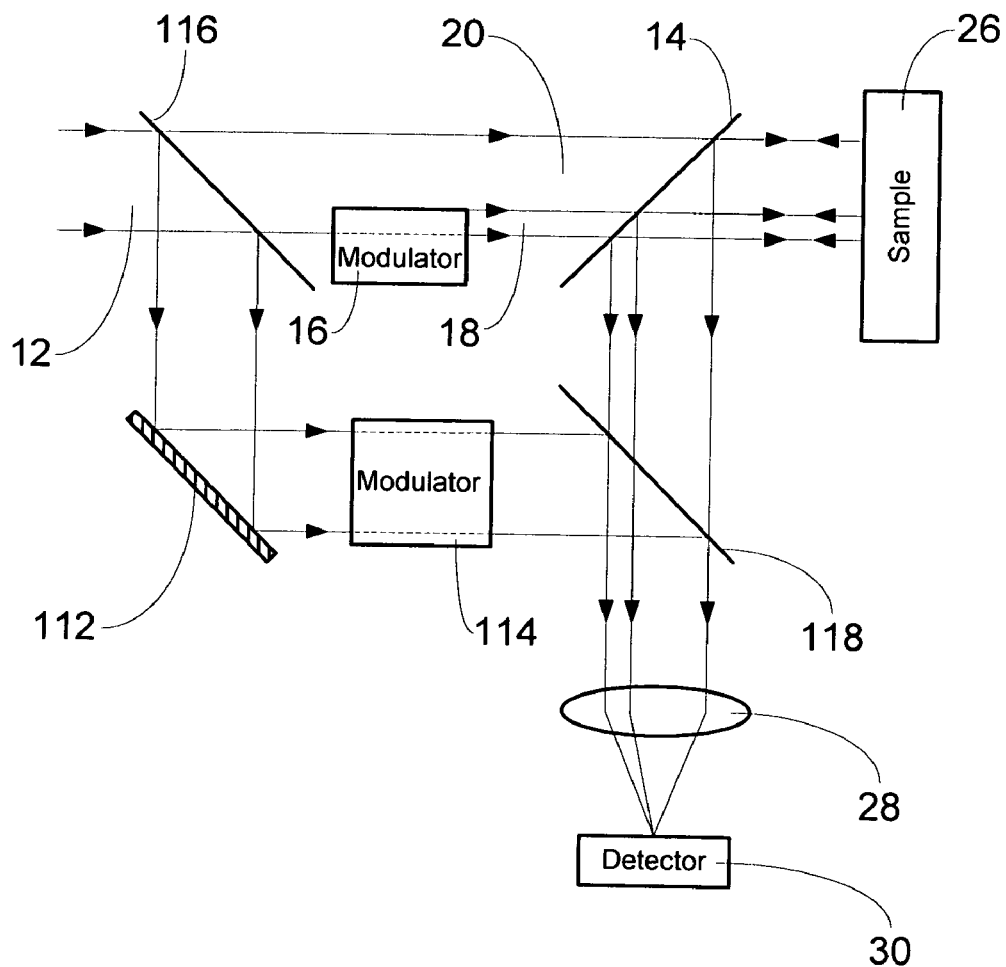
FIG. 7 is a schematic diagram showing an embodiment utilizing a Mach-Zehnder interferometer according to the invention.

In the above embodiments (except FIG. 6), a Michelson interferometer is used, in which the beam splitter or fiberoptic coupler has two functions: splitting and combining beams. FIG. 7 shows schematically another embodiment employing a different interferometer, a Mach-Zehnder interferometer.

As shown in FIG. 7, a Mach-Zehnder interferometer uses two splitters 116 and 118 to split and combine beams, respectively. Beam 12 is split into reference and sample beams. The reference beam is reflected by splitter 116, then by a reflector 112. Then it is transmitted through a phase modulator 114, which tunes the path length of the reference beam, and is reflected by splitter 118. The sample beam passes through splitter 116 and is divided into portions 18 and 20 by modulator 16. It then passes through splitter 14 and impinges onto sample 26. The reflected sample beam is reflected by splitter 14 and passes through splitter 118 to combine with the reference beam.

Due to modulators 16 and 114 and low coherence interference, the reference beam interferes only with portion 18. Thus this embodiment achieves the same results as the embodiment of FIG. 1.

FIG. 8—DEVICE HAVING FIXED REFERENCE REFLECTORS AND MODULATOR

Figure 8:
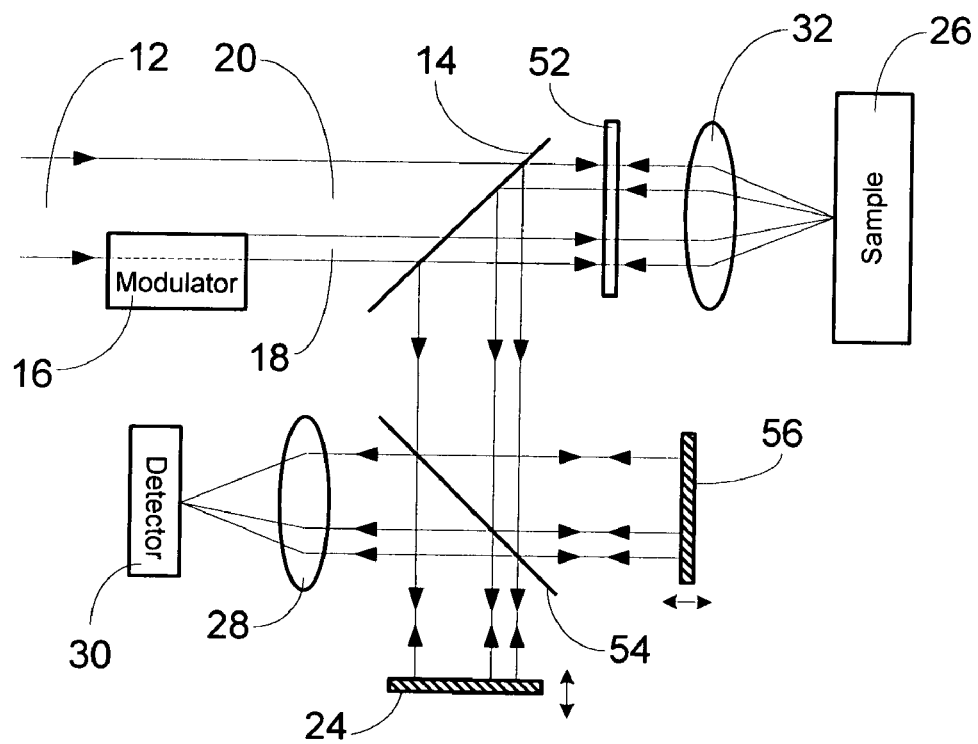
FIG. 8 is a schematic diagram showing an embodiment having fixed reference reflector and modulator according to the invention.

FIG. 8 shows a device that is different from the above embodiments. Here a reference path length can also match a sample path length when its reference reflector and spatial phase modulator are fixed, as is shown schematically. Beam 12 is divided into portions 18 and 20 and passes through splitter 14. Then part of the beam is reflected as a reference beam by a partial reflector 52, which serves as a fixed reference reflector. The rest of the beam, as a sample beam, passes through reflector 52 and is focused on sample 26. The reflected sample beam passes through reflector 52 again and joins the reference beam. Both the sample and reference beams are reflected by splitter 14 and then enter a Michelson interferometer, which is constructed by a beam splitter 54 and adjustable reflectors 24 and 56.

If the paths of the sample beam, which have reflections between reflector 52 and sample 26, are omitted because of reduced intensity, each of the reference and sample beams contains two optical paths before impinging on splitter 54. For example, the sample beam has two paths resulting from portions 18 and 20, of which the former is of interest. In the Michelson interferometer, the beams are split and combined by splitter 54. They also travel to and are reflected by reflectors 24 and 56. The combined beams are focused on detector 30.

Thus for the reference and sample beams, each has four optical paths from the light source (not shown in FIG. 8) to detector 30 and there are total eight paths. The eight paths depend on modulator 16 and the positions of reflectors 52, 24, and 56. Since modulator 16 and partial reflector 52 are fixed, reflectors 24 and 56 are adjusted to match the reference and sample path lengths. Assume that the distance between reflector 52 and sample 26 is much larger than the beam's coherence length and so is path length difference between portions 18 and 20. When the lengths are matched between the reference path containing portion 20 and the sample path containing portion 18, all other path length differences are larger than the beam's coherence length. Thus beam portion 18 can be used as a virtual beam as in the other embodiments.

FIG. 9—DEVICE HAVING PHASE DELAYED BEAM PORTION AS REFERENCE BEAM

Figure 9:
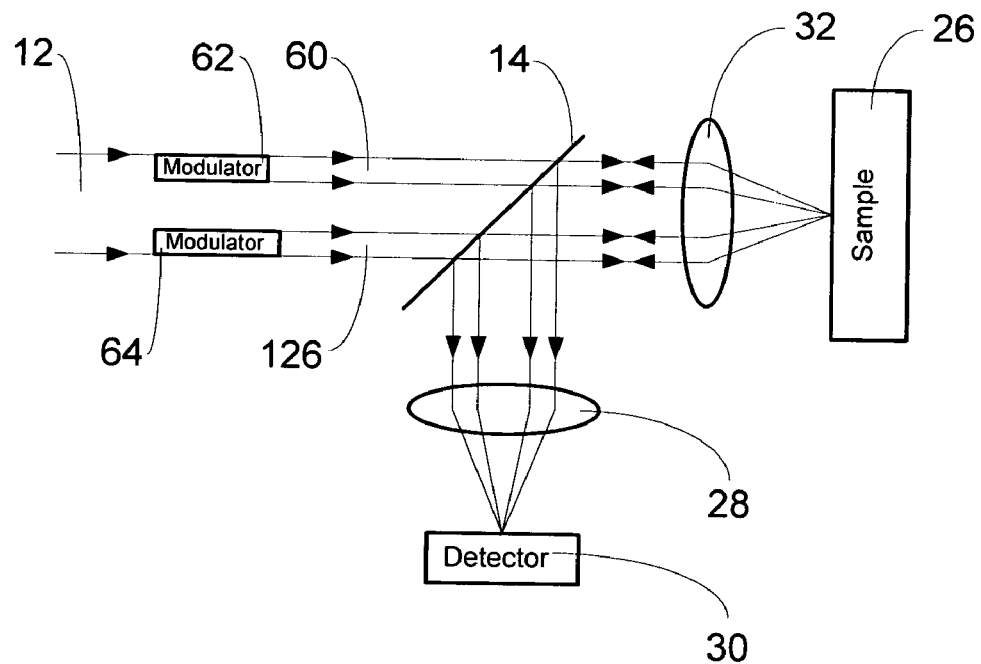
FIG. 9 is a schematic diagram showing an embodiment which utilizes a phase delayed beam portion as a reference beam according to the invention.

FIG. 9 illustrates schematically another embodiment. Beam 12 is processed by spatial phase modulators 62 and 64, which phase delay beam portions 60 and 126, respectively. After that, the beam is transmitted through splitter 14 and is focused on a surface area of sample 26. Portions 60 and 126, as virtual beams, are focused on two virtual beam spots (not shown in FIG. 9) on the surface. The reflected beam from the surface is collimated, reflected by splitter 14, and focused on detector 30 for interference.

Thanks to substantial phase delays on portions 60 and 126, when the portions interfere with each other, they don't interfere with the rest of the beam. The path length difference of the two portions is determined by the modulators and the surface profile. Thus the relative height between the two virtual beam spot areas is obtained when the two path lengths are matched by tuning the modulators. With a scanning mechanism, the embodiment of FIG. 9 can be used as a surface profiler. The resulting surface profiler has improved lateral resolution due to the virtual beam spots. Since portions 60 and 126 have side-by-side paths, the profiler is vibration-insensitive.

FIGS. 10-A–10-C—DEVICES HAVING ADDITIONAL LENS SYSTEM FOR RECEIVING REFLECTION FROM SAMPLE

FIG. 10-A shows schematically another embodiment. A spatial phase modulator 128 produces a phase delayed beam portion 72 out of beam 12. The beam is then focused on sample 26 by a lens system 68. The reflected beam is received and collimated into a beam 66 by another lens system 70. When beam 66 is coupled with a reference beam (not shown in FIG. 10-A), interference occurs exclusively between portion 72 and the reference beam due to the phase delay. Applications of this embodiment include scanning optical microscopes. Portion 72 creates a virtual beam spot on a surface or a virtual volume in a highly scattering medium. In the case of virtual volume, layered information can be obtained through a method similar to an OCT's. The virtual spot or volume improves lateral resolution in measurements.

Another embodiment is shown schematically in FIG. 10-B. A spatial phase modulator 80 is added to the embodiment of FIG. 10-A. Modulator 80 phase delays a portion 82 of the reflected beam which is beam 66 in FIG. 10-A. Because as portion 72, portion 82 has its corresponding virtual beam spot on sample 26, there is an overlap of the two virtual beam spots. FIG. 10-C shows schematically an overlapping area 90, where it is assumed that virtual beam spots 86 and 88 correspond to portions 72 and 82, respectively. Area 90 actually is related to an overlap of beam portions 72 and 82, or in other words, the part of the beam which is phase delayed by both modulators.

Therefore the embodiment of FIG. 10-B creates a detectable area smaller than the virtual beam spot and improves lateral resolution further. Similar principles, apply to an overlap of two virtual volumes.

The function of modulator 80 shows that the embodiment of FIG. 10-A has the same result of improved lateral resolution if the beam propagation direction is reversed.

FIG. 11-A and B—DEVICES WITH SIMPLE STRUCTURES

An embodiment with a relatively simple structure is shown schematically in FIG. 11-A. A light source 96 emits a divergent beam 108 from an emitting spot and a detector 98 detects radiation with a light detecting spot (the spots are not shown in FIG. 11-A). Detector 98 is disposed adjacent to source 96. A beam portion 106 is reflected back to its origin by a reference reflector 104 and functions as a reference beam. A beam portion 102 is phase delayed by a spatial phase modulator 100 and impinges onto sample 26. Part of the reflected portion 102 is transmitted through modulator 100 again and converges to the origin, where portion 106 and part of portion 102 combine and interfere with each other exclusively. Assume that the detecting spot is close enough to the emitting spot to sense the interference signals.

With reference to FIG. 11-A, source 96 and detector 98 may be replaced by a fiberoptic configuration, which is shown schematically in FIG. 11-B. The fiberoptic configuration is similar to that employed in FIG. 6. A light source and detector (not shown in FIG. 11-B) are coupled to fibers 46 and 48, respectively. Coupler 44 couples fiber 42 to fibers 46 and 48. Fiber 42 emits beam 108 and receives the reflected beam portions.

CONCLUSION, RAMIFICATIONS, AND SCOPE

Accordingly, the reader will see that a beam portion, created by wavefront division and phase delayed, can be used as a virtual beam inside a sample beam through interference with the reference beam. The virtual beam is insensitive to the lateral misalignment and improves lateral resolution of scanning optical microscopes, scanning optical profilers, readout systems in optical data storage, and OCTs.

Although the description above contains many specificities, these should not be construed as limiting the scope of the invention but as merely providing illustrations of some of the presently preferred embodiments. Numerous modifications, alternations, and variations will be obvious to those skilled in the art.

For example, when the axial resolution isn't a critical concern, like in the case of a scanning optical microscope, a beam is not restricted to a short coherence length type. The purpose is to obtain interference exclusively between a phase delayed beam portion and a reference beam. Thus a beam with a longer coherence length just requires a beam portion that has a relatively longer phase delay.

In FIG. 6, coupler 44 can be replaced by a fiberoptic circulator, which allows a beam to be transmitted from fiber 46 to 42, and from fiber 42 to 48 only. The circulator roughly quadruples the signal power since coupler 44 totally splits the beam twice. Again in FIG. 6, the embodiment can be changed to a free-space type by employing a collimated beam from a light source and replacing the coupler, the fibers, and lens system 38 by a beam splitter. In FIGS. 5 and 6, lens systems 32 and 38 can be replaced by a single lens system, which focuses a beam from fiber 42 on sample 26. In this embodiment, a new spatial phase modulator is required for processing a divergent or a convergent beam and so are reflectors 110 and 136.

In FIG. 8, partial reflector 52 doesn't need to cover the whole beam as long as it generates a desired reference beam. And the Michelson interferometer, which matches reference and sample path lengths, can be replaced by a Mach- Zehnder interferometer or other types of interferometers which create a pair of mismatching path lengths.

The embodiments of FIGS. 9 and 3 can be combined to form a device which functions both as a microscope and profiler. For example, reflector 24 can be added on the other side of splitter 14 opposing lens system 28 in FIG. 9. When working as a scanning microscope, its two virtual beams correspond to two sample paths. Reflector 24 is adjusted to match a reference to two sample path lengths separately. For a certain scanning speed, the more spots it can measure at each position, the faster the measurement speed.

In FIGS. 10-A and 10-B, lens system 70 and modulator 80 can be disposed on the other side of sample 26 to collect and process the transmissive sample beam. Here sample 26 is preferably thin and at least partially transparent. The transmissive sample beam can be utilized in the same way as reflective sample beam 66.

Lastly in FIG. 11-A, a lens system can be added between source 96 and sample 26. The lens system focuses part of beam 108 on sample 26. It improves lateral resolution, increases signal power, and provides more scanning options. Also in FIG. 11-A, a tuning mechanism can be added to adjust the reference path length.

In all embodiments the nature of the sample and the beam, the light wavelength, and the remaining components can be changed from the exemplary one discussed and selected and chosen as we see in the above.

Therefore the scope of the invention should be determined by the appended claims and their legal equivalents, rather than by the examples given.

The invention claimed is:

1. An interferometric optical device comprising:
   1) a light source for generating a first beam;
   2) splitting means for splitting said first beam into a reference and a sample beam;
   3) a spatial phase modulator for dividing said sample beam into a plurality of beam portions by wavefront division and producing phase shift on at least one of said beam portions, said phase-shifted beam portion being arranged to remain within said sample beam; and
   4) a detector for sensing interference between said reference beam and said phase-shifted portion,
   whereby said phase-shifted beam portion is used as a virtual beam in applications.

2. The optical device according to claim 1 wherein said light source has relatively low coherence with respect to a coherent light source.

3. The optical device according to claim 1 wherein said reference and sample beams are generated by splitting said first beam through wavefront division.

4. The optical device according to claim 1, further including tuning means for tuning path length difference between said reference beam and said phase-shifted beam portion.

5. The optical device according to claim 1, further including at least one medium for receiving and transmitting said sample beam.

6. The optical device according to claim 5, further including scanning means and data processing means for obtaining an image of said medium.

7. The optical device according to claim 5, further including lens means for focusing said sample beam on said medium.

8. The optical device according to claim 1, further including combining optics for combing said reference and sample beams.

9. The optical device according to claim 1 wherein said spatial phase modulator includes a plurality of subordinate spatial phase modulators, said subordinate spatial phase modulators being disposed in predetermined locations for processing said sample beam respectively.

10. The optical device according to claim 1, further including at least one optical fiber for transmitting said reference and sample beams.

11. A method for generating optical interference, comprising:
   1) providing a light source for generating a first beam;
   2) creating a reference and a sample beam from said first beam;
   3) disposing a spatial phase modulator for dividing said sample beam into a plurality of beam portions by wavefront division and phase shifting at least one of said beam portions, said phase-shifted beam portion being arranged to remain within said sample beam; and
   4) sensing interference caused by said reference beam and said phase-shifted beam portion by a detector,
   whereby said phase-shifted beam portion is used as a virtual beam in applications.

12. The method according to claim 11 wherein said light source has relatively low coherence with respect to a coherent light source.

13. The method according to claim 11, further including tuning the optical path length difference between said reference beam and said phase-shifted beam portion.

14. The method according to claim 11, further including at least one medium for receiving and transmitting said sample beam.

15. The method according to claim 14, further including focusing said sample beam onto said medium.

16. The method according to claim 14, further including scanning said medium and processing the acquired data for obtaining an image of said medium.

17. The method according to claim 11, further including combining said reference and sample beams.

18. A method for generating optical interference, comprising:
   1) causing a light source to generate a beam;
   2) providing a spatial phase modulator for dividing said beam into at least three beam portions by wavefront division and phase shifting at least two of said beam portions, said phase-shifted beam portions being arranged to remain within said beam;
   3) transmitting said beam including said phase-shifted beam portions to a detector; and
   4) sensing interference caused by said phase-shifted beam portions by said detector,
   whereby said phase-shifted beam portions are used as virtual beams in applications.

19. The method according to claim 18, further including arranging said sample beam to impinge onto a medium.

20. The method according to claim 19, further including scanning said medium and processing the acquired data for obtaining an image of said medium.

21. The method according to claim 18 wherein said light source has relatively low coherence with respect to a coherent light source.

22. The method according to claim 18, further including tuning phase shift of at least one of said phase-shifted beam portions.

* * * * *